United States Patent [19]

Bürstinghaus et al.

[11] Patent Number: 4,612,306
[45] Date of Patent: Sep. 16, 1986

[54] OXIMINOPHOSPHORIC ACID DERIVATIVES AND THEIR USE FOR CONTROLLING PESTS

[75] Inventors: Rainer Büerstinghaus, Weinheim; Erhard Henkes, Einhausen; Karl Kiehs, Lampertheim; Heinrich Adolphi, Limburgerhof, all of Fed. Rep. of Germany

[73] Assignee: BASF Aktiengesellschaft, Ludwigshafen, Fed. Rep. of Germany

[21] Appl. No.: 696,789

[22] Filed: Jan. 31, 1985

[30] Foreign Application Priority Data

Jan. 31, 1984 [DE] Fed. Rep. of Germany ....... 3403203

[51] Int. Cl.$^4$ .......................... A01N 57/04; C07F 9/16
[52] U.S. Cl. ...................... 514/112; 558/168
[58] Field of Search ........................ 260/940; 514/112; 558/168

[56] References Cited

U.S. PATENT DOCUMENTS 4,424,215  1/1984  Buerstinghaus et al. ............ 260/940

*Primary Examiner*—Anton H. Sutto
*Attorney, Agent, or Firm*—Keil & Weinkauf

[57] ABSTRACT

Oximinophosphoric acid derivatives of the formula I

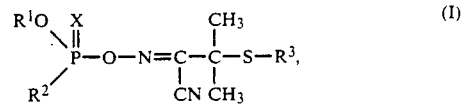

where
- $R^1$ is straight-chain or branched alkyl of not more than 4 carbon atoms,
- $R^2$ is straight-chain or branched alkoxy or alkylthio, each of not more than 4 carbon atoms, straight-chain or branched alkyl of not more than 3 carbon atoms, phenyl, amino, or straight-chain or branched alkylamino or dialkylamino, where alkyl in each case is of not more than 4 carbon atoms,
- $R^3$ is straight-chain or branched alkyl of not more than 4 carbon atoms and X is oxygen or sulfur, their preparation, and their use as crop protection agents.

7 Claims, No Drawings

OXIMINOPHOSPHORIC ACID DERIVATIVES AND THEIR USE FOR CONTROLLING PESTS

The present invention relates to oximinophosphoric acid derivatives, a process for their preparation, pesticides which contain these phosphoric acid derivatives as active ingredients, and a method for controlling pests with these active ingredients.

Oximinophosphoric acid derivatives are disclosed in German Published Applications DAS No. 1,052,981 and DAS No. 1,238,902 and German Laid Open Applications DOS Nos. 2,304,848, 2,952,738 and 3,135,182. They are useful for controlling insects and arachnids, but their action is not always completely satisfactory, especially where low concentrations are used.

We have found that oximinophosphoric acid derivatives of the formula I $$\begin{array}{c} R^1O \\ \diagdown \\ R^2 \end{array} \!\! \overset{X}{\underset{\|}{P}} \!\! - O - N = C - \underset{\underset{CH_3}{|}}{\overset{\overset{CH_3}{|}}{C}} - S - R^3, \quad (I)$$

where
- $R^1$ is straight-chain or branched alkyl of not more than 4 carbon atoms,
- $R^2$ is straight-chain or branched alkoxy or alkylthio, each of not more than 4 carbon atoms, straight-chain or branched alkyl of not more than 3 carbon atoms, phenyl, amino, or straight-chain or branched alkylamino or dialkylamino, where alkyl in each case is of not more than 4 carbon atoms,
- $R^3$ is straight-chain or branched alkyl of not more than 4 carbon atoms and X is oxygen or sulfur, possess very good insecticidal, acaricidal and nematicidal activity and are superior to conventional active ingredients having a similar structure or the same direction of action.

The oximinophosphoric acid derivatives of the formula I can be obtained by reacting an appropriate α-oximinonitrile with an appropriate (thiono)(thiol) phosphoric (phosphonic) ester (amide) halide:

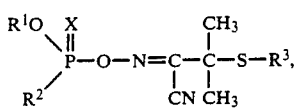

$$\begin{array}{c} CH_3 \\ | \\ H-O-N=C-C-S-R^3 \\ | \quad | \\ CN \; CH_3 \end{array} + \begin{array}{c} R^1O \quad X \\ \diagdown \!\! \overset{\|}{P} - Hal \\ R^2 \end{array} \xrightarrow{-HHal}$$

(II)       (III)

$$\begin{array}{c} R^1O \\ \diagdown \\ R^2 \end{array} \!\! \overset{X}{\underset{\|}{P}} \!\! - O - N = C - \underset{\underset{CH_3}{|}}{\overset{\overset{CH_3}{|}}{C}} - S - R^3$$

(I)

For economic reasons, halogen (Hal) is preferably chlorine.

The reaction is advantageously carried out in a solvent or diluent, suitable examples being aliphatic and aromatic hydrocarbons and chlorohydrocarbons, such as petroleum ether, benzene, toluene, xylene, gasoline, dichloromethane, chloroform, tetrachloromethane, 1,2-dichloroethane or chlorobenzene, ethers, such as diethyl ether, di-n-butyl ether, methyl tert.-butyl ether, tetrahydrofuran or dioxane, ketones, e.g. acetone, methyl ethyl ketone or methyl isopropyl ketone, and nitriles, such as acetonitrile or propionitrile. Mixtures of these substances can also be used as solvents or diluents.

Suitable acid acceptors are the basic agents conventionally used in the phosphorylation of hydroxy compounds. Particularly useful are alkali metal carbonates and alcoholates, such as sodium carbonate, potassium carbonate, sodium methylate, potassium methylate, sodium ethylate or potassium ethylate, and aliphatic, aromatic and heterocyclic amines, e.g. triethylamine, dimethylamine, piperidine, dimethylaniline, dimethylbenzylamine or pyridine. In some cases, it is advantageous to use an alkyl-lithium compound, e.g. n-butyl-lithium, or an alkali metal hydride, e.g. sodium hydride.

Instead of adding an acid acceptor, it is also possible to prepare the salts of the α-oximinonitriles (II), e.g. the alkali metal, alkaline earth metal or ammonium salts, before the reaction, and to react these.

The starting materials are usually employed in stoichiometric amounts, but an excess of one or other of the starting materials may be entirely advantageous in specific cases.

The reaction usually takes place at an adequate rate at above room temperature. In general, the temperature must not exceed 120° C. Since in some cases the reaction takes place with production of heat, it may be advantageous to provide a means of cooling.

The novel active ingredient is recovered from the reaction mixture in a conventional manner, for example by the addition of water, separation of the phases and distillation and/or column chromatography.

The α-oximinonitriles of the formula (II) which are used as starting materials for the preparation of compounds of the formula (I) are novel substances. They can be prepared by, for example, reacting a halogenated α-oximinonitrile of the formula (IV), where Hal is, for example, chlorine or bromine, with an alkylthiol of the formula (V) according to the following equation:

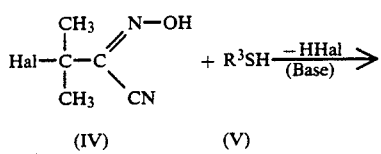

(IV)      (V)

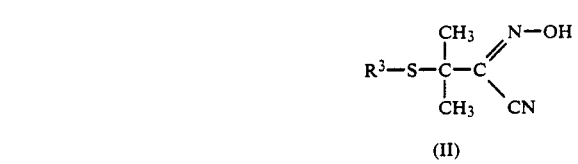

(II)

Suitable acid acceptors are the basic agents conventionally used in reactions for introducing alkylthiol groups into halogen compounds. Particularly suitable compounds are alkali metal hydroxides and alcoholates, such as sodium hydroxide, potassium hydroxide, sodium methylate, potassium methylate, sodium ethylate or potassium ethylate, and aliphatic, aromatic and heterocyclic amines. In some cases, it is advantageous to use an alkyl-lithium compound, e.g. n-butyl-lithium, or an alkali metal hydride, e.g. sodium hydride.

Instead of adding an acid acceptor, it is also possible to prepare the salts of the alkylthiols, e.g. the alkali metal salts, before the reaction, and to react these.

α-oximinonitriles of the formula (IV) are obtained in a conventional manner (Houben-Weyl, Methoden der organischen Chemie, Volume IV/5a, page 143 et seq, Stuttgart 1975), by halogenation of the precursor VI disclosed in U.S. Pat. No. 4,302,402:

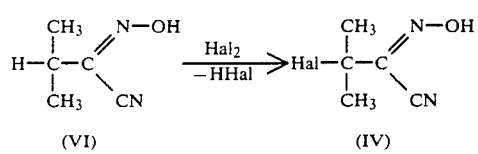

The (thio)(thiol) phosphoric (phosphonic) ester (amide) halides III furthermore required for the synthesis of the compounds of the formula I are disclosed in Houben-Weyl, Methoden der organischen Chemie, Volume XII/2, page 274 et seq, (Stuttgart 1964), and can be prepared by the synthesis routes described there.

Some of the novel compounds of the formula I are obtained in the form of colorless or slightly brownish oils, which can be freed from the final volatile constituents by prolonged heating at moderately elevated temperatures under reduced pressure (incipient distillation), and purified in this manner. Where the compounds of the formula I are crystalline, they can be purified by recrystallization.

Since the compounds of the formula I generally occur as mixtures of syn and antistructural isomers, their melting or boiling points are of little use with regard to identification, unless the structural isomers have been separated beforehand. H-NMR spectra, the results of elemental analysis and IR spectra with typical absorption maxima from the fingerprint region inbetween 1500 cm$^{-1}$ and 900 cm$^{-1}$ are therefore given below for each of the substances prepared.

EXAMPLE 1

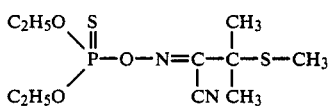

6.0 g of 2-hydroximino-3-methylthio-3-methylbutyronitrile and 5.2 g of powdered potassium carbonate are dissolved or suspended in 60 ml of acetonitrile, and 7.52 g of O,O-diethyl thiophosphorochloridate are added dropwise, while stirring. The mixture is stirred for 24 hours at 60° C., after which insoluble constituents are filtered off under suction, and the filtrate is evaporated down under reduced pressure. The residue is taken up in ether, and the solution is washed once with 5% strength sodium hydroxide solution and three times with water, and freed from solvent. After incipient distillation at 75° C. and under 0.01 mbar, 11.45 g (yield 97% of theory) of O-(O,O-diethylthiophosphoryl)-2-oximino-3-methyl-thio-3-methylbutyronitrile remain as a virtually colorless viscous oil.

$C_{10}H_{19}N_2O_3PS_2$ (310)

Calculated: C: 38.7 H: 6.2 N: 9.0; Found: C: 39.0 H: 6.4 N: 9.2. 200-MHz-H-NMR-spectrum in CDCl$_3$ (δ values in ppm): 1.35 (t, 6H); 1.65 (s, 6H); 2.05 (s, 3H); 4.20–4.45 (m, 4H).

Infrared absorptions (cm$^{-1}$): 1108, 1022, 975, 928, 900, 854, 824, 800, 764.

Where one or more physical data for their identification are given, the compounds listed in the table below are likewise prepared by the method described in Example 1; other compounds of the formula (I) can be obtained in the same manner, with appropriate modification of the methods according to the particular amount required and, if necessary, after a preliminary experiment (to determine the best reaction conditions).

TABLE

| Ex. No. | R$^1$ | R$^2$ | R$^3$ | X | IR-Absorption (Maximum at cm$^{-1}$) |
|---|---|---|---|---|---|
| 2 | CH$_3$ | CH$_3$O | CH$_3$ | S | 1443, 1181, 1109, 1037, 927, 901, 862, 828, 766 |
| 3 | CH$_3$ | CH$_3$O | CH$_3$ | O | |
| 4 | C$_2$H$_5$ | C$_2$H$_5$O | CH$_3$ | O | 1296, 1032, 930 |
| 5 | C$_2$H$_5$ | n-C$_3$H$_7$S | CH$_3$ | S | 1021, 962, 923, 888, 844, 789, 760 |
| 6 | C$_2$H$_5$ | n-C$_3$H$_7$S | CH$_3$ | O | |
| 7 | C$_2$H$_5$ | sec.-C$_4$H$_9$S | CH$_3$ | S | |
| 8 | C$_2$H$_5$ | sec.-C$_4$H$_9$S | CH$_3$ | O | 1440, 1380, 1369, 1263, 1133, 1102, 1020, 919, 895 |
| 9 | C$_2$H$_5$ | i-C$_3$H$_7$NH | CH$_3$ | O | 1254, 1140, 1047, 939, 907, 771 |
| 10 | C$_2$H$_5$ | NH$_2$ | CH$_3$ | O | |
| 11 | C$_2$H$_5$ | CH$_3$ | CH$_3$ | S | 1300, 1036, 968, 936, 910, 886, 795, 756 |
| 12 | C$_2$H$_5$ | C$_2$H$_5$ | CH$_3$ | S | 1045, 1023, 962, 928, 887, 841, 809, 798 |
| 13 | CH$_3$ | C$_2$H$_5$ | CH$_3$ | S | 1458, 1053, 886, 814 |
| 14 | C$_2$H$_5$ | C$_6$H$_5$ | CH$_3$ | S | 1439, 1123, 1034, 1026, 886, 749 |
| 15 | C$_2$H$_5$ | i-C$_4$H$_9$ | CH$_3$ | S | |
| 16 | C$_2$H$_5$ | C$_2$H$_5$O | C$_2$H$_5$ | S | 1108, 1022, 976, 927, 901, 854, 824, 799, 765 |
| 17 | C$_2$H$_5$ | C$_2$H$_5$O | C$_2$H$_5$ | O | 1292, 1166, 1108, 1033, 987, 931, 906, 774 |
| 18 | C$_2$H$_5$ | C$_2$H$_5$ | C$_2$H$_5$ | S | 1045, 1023, 963, 927, 887, 841, 809, 798, 767 |
| 19 | C$_2$H$_5$ | CH$_3$ | C$_2$H$_5$ | S | 1108, 1037, 969, 936, 910, 887, 795, 758 |
| 20 | CH$_3$ | CH$_3$O | C$_2$H$_5$ | S | 1181, 1109, 1039, 929, 902, 863, 831, 767 |
| 21 | CH$_3$ | CH$_3$O | C$_2$H$_5$ | O | |
| 22 | C$_2$H$_5$ | i-C$_3$H$_7$S | C$_2$H$_5$ | O | |
| 23 | C$_2$H$_5$ | n-C$_3$H$_7$S | C$_2$H$_5$ | O | |
| 24 | C$_2$H$_5$ | C$_2$H$_5$O | i-C$_3$H$_7$ | S | 1107, 1051, 1024, 976, 928, 900, 855, 824 |
| 25 | C$_2$H$_5$ | C$_2$H$_5$O | t-C$_4$H$_9$ | S | 1163, 1105, 1024, 976, 927, 897, 855, 825 |
| 26 | C$_2$H$_5$ | sec.-C$_4$H$_9$S | C$_2$H$_5$ | S | |
| 27 | C$_2$H$_5$ | n-C$_3$H$_7$S | C$_2$H$_5$ | S | |
| 28 | C$_2$H$_5$ | n-C$_3$H$_7$S | i-C$_3$H$_7$ | S | |
| 29 | C$_2$H$_5$ | n-C$_3$H$_7$S | t-C$_4$H$_9$ | S | |

Intermediates

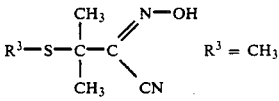

40.5 g of 2-hydroximino-3-methylbutyronitrile are dissolved in 750 ml of methylene chloride, and 57.9 g of bromine, dissolved in 70 ml of methylene chloride, are added in the course of 23 hours with exposure to light (HPK 125 W lamp). The resulting mixture is added dropwise to a solution of sodium methyl mercaptide (prepared by passing 24 g of methyl mercaptan in gaseous form into 30% strength sodium methylate). Stirring is carried out for 12 hours at room temperature, the solvent is stripped off under reduced pressure, the residue is taken up in ether, and the solution is washed three times with water and dried over sodium sulfate. The solution is filtered over silica gel and the filtrate is evaporated down. The oil which remains is distilled under reduced pressure (0.01 mbar), and 10.2 g of the desired product 2-hydroximino-3-methylthio-3-methylbutyronitrile pass over as a colorless liquid at 86° C.; on cooling this liquid crystallizes through to give a product having a melting range of 61°–64° C.

Infrared absorptions (cm$^{-1}$); 1423, 1387, 1104, 1016, 982, 680, 640.

60 MHz-NMR-spectrum in CDCl$_3$ ($\delta$ values in ppm): 1.60 (s, 6H); 2.0 (s 3H); 9.35 (broad s, 1H).

The intermediates (II) listed in the table below are likewise obtained by the method described above; other intermediates of the formula II can be obtained in the same manner, with appropriate modification of the methods according to the particular amount required and, if necessary, after a preliminary experiment to determine the best reaction conditions.

| R$^3$ | IR Absorption (Maximum at cm$^{-1}$) |
|---|---|
| C$_2$H$_5$ | 1447, 1425, 1387, 1138, 1103, 983 |
| i-C$_3$H$_7$ | 1455, 1444, 1424, 1387, 1368, 1138, 1005, 989 |
| n-C$_3$H$_7$ | |
| t-C$_4$H$_9$ | 1425, 1366, 1156, 1135, 1006, 987, 685 |

The phosphates of the formula I can be used for effectively controlling pests from the classes comprising the insects, arachnids and nematodes, and can be employed as pesticides in crop protection, in the hygiene and veterinary sectors and for the protection of stored materials.

The formulations contain in general from 0.1 to 95, preferably from 0.5 to 90, % by weight of active ingredient.

The concentrations of active ingredient in the ready-to-use formulations can be varied within a wide range. In general, they are from 0.00001 to 10%, preferably from 0.001 to 0.1%.

The active ingredients can also be used very successfully by the ultra-low-volume method (ULV), in which it is possible to apply formulations containing more than 95% by weight of active ingredient, or even to apply the active ingredient without additives.

The application rate for the active ingredient under open air conditions is from 0.02 to 10, preferably from 0.1 to 2.0, kg/ha.

Oils of various types, herbicides, fungicides, other pesticides, and bactericides can be added to the active ingredients, if necessary even directly before use (tank mix). These agents can be mixed with the agents according to the invention in a weight ratio of from 1:10 to 10:1.

Contact action on house flies (Musca domestica), application test

1 $\mu$l of the active ingredient in solution in acetone is applied to the ventral abdomen of 4-day old imagoes lightly anesthetized with CO$_2$. A micrometer syringe is used for this purpose.

Groups of 20 test animals treated in the same manner are introduced into cellophane bags (about 500 ml).

After 4 hours, the number of animals which have been knocked down is counted, and the LD 50 is determined graphically.

Result:
Active ingredient of Example 1: LD 50 0.08 $\mu$g/fly
malathion: LD 50 0.5 $\mu$g/fly Tribolium castaneum; malathion-resistant The contact action is tested on treated circular filter papers of 7 cm diameter, and the mortality is determined after 24 hours.

| Active ingredient of Example 1 | 0.1 mg | 100% mortality |
|---|---|---|
| malathion | 2.0 mg | ineffective. |

Prodenia litura, growth test

This test is carried out using caterpillars from the third larval stage onward, on treated agar nutrient medium.

| Active ingredient of Example 1 | 1 ppm | 100% mortality. |
|---|---|---|

For the following examples, the compounds below from German Laid-Open Application DE-OS No. 31 35 182 were used for comparison purposes:

$$\begin{array}{c} CH_3-O \\ \phantom{CH_3-O} \diagdown \\ \phantom{CH_3-O} \phantom{O}P \\ \phantom{CH_3-O} \diagup \\ CH_3-O \end{array} \begin{array}{c} S \\ \| \\ \phantom{P} \end{array} -O-N=C-\overset{CN}{\underset{CH_3}{\overset{|}{C}}}-O-C_2H_5 \qquad I$$

and $$\begin{array}{c} C_2H_5-O \\ \phantom{C_2H_5-O} \diagdown \\ \phantom{C_2H_5-O} \phantom{O}P \\ \phantom{C_2H_5-O} \diagup \\ {}_nC_3H_7-S \end{array} \begin{array}{c} S \\ \| \\ \phantom{P} \end{array} -O-N=C-\overset{CN}{\underset{CH_3}{\overset{|}{C}}}-O-C_2H_5 \qquad II$$

1. Continuous contact action on houseflies (Musca domestica)

The insides of Petri dishes 10 cm in diameter are treated with an acetonic solution of the active ingredients.

After the solvent has evaporated, 20 4-day old houseflies are placed in each dish.

The kill rate is determined after 4 hours.
Results:

| | | Kill rate |
|---|---|---|
| Example 1 | 0.01 mg | 100% |
| Example 12 | 0.01 mg | 100% |
| Example 13 | 0.01 mg | 100% |
| Example 16 | 0.01 mg | 100% |
| Example 17 | 0.01 mg | 100% |
| Example 18 | 0.01 mg | 100% |
| Example 20 | 0.01 mg | 100% |
| Example 25 | 0.004 mg | 80% |
| Comparative agent I | 0.02 mg | 100% |
| | 0.01 mg | <60% |
| Comparative agent II | 0.02 mg | 100% |
| | 0.01 mg | <60% |

2. Contact action on oriental cockroaches (Blatta orientalis)

The bottom of 1 liter preserving jars is treated with an acetonic solution of the active ingredients.

After the solvent has evaporated, 5 adult cockroaches are introduced into each jar.

The kill rate is determined after 48 hours.
Results:

| | | Kill rate |
|---|---|---|
| Example 1 | 0.02 mg | 100% |
| Example 16 | 0.04 mg | " |
| Comparative agent I | 0.1 mg | " |
| | 0.04 mg | <60% |

-continued

|  | Kill rate |  |
|---|---|---|
| Comparative agent II | 0.1 mg | 100% |
|  | 0.04 | <60% |

3. Contact action on mosquito larvae (Aedes aegypti)

The active ingredient formulations are added to 200 ml of tapwater, and 30–40 mosquito larvae of the fourth larval stage are introduced.

The temperature is kept at 20° C. The action is determined after 24 hours.

Results:

|  |  | Kill rate |
|---|---|---|
| Example 1 | 0.01 mg | 100% |
| Example 2 | 0.2 mg | " |
| Example 16 | 0.04 mg | " |
| Example 17 | 0.02 mg | " |
| Example 18 | 0.1 mg | " |
| Example 20 | 0.1 mg | " |
| Example 24 | 0.04 mg | " |
| Example 25 | 0.04 mg | " |
| Comparative agent I | 1 ppm | <60% |
| Comparative agent II | 1 ppm | <60% |

4. Breeding experiment with housefly larvae (Musca domestica)

4.5 ml of skimmed milk is filled into 50 ml penicillin flasks, and 0.5 ml of the aqueous active ingredient formulations is added. After brief mixing, a ball of absorbent cotton is introduced and about 50 egg larvae of the housefly are placed on each ball.

The flasks are covered and kept at room temperature. The development is assessed after 7 days.

Results:

|  |  | Kill rate |
|---|---|---|
| Example 1 | 1.0 ppm | 100% |
| Example 9 | 0.2 ppm | " |
| Example 12 | 0.1 ppm | " |
| Comparative agent I | 2.5 ppm | " |
|  | 1.0 ppm | <60% |
| Comparative agent II | 2.5 ppm | 100% |
|  | 1.0 ppm | <60% |

5. Contact action on cotton stainers (Dydercus intermedius)

Petri dishes 10 cm in diameter are lined with 1 ml of acetonic active ingredient solutions.

After evaporation of the solvent, 20 larvae of the penultimate stage are introduced into each dish, and the action is assessed after 24 hours.

Results:

|  |  | Kill rate |
|---|---|---|
| Example 1 | 0.002 mg | 100% |
| Example 2 | 0.004 mg | " |
| Example 11 | 0.002 mg | 80% |
| Example 12 | 0.002 mg | " |
| Example 16 | 0.002 mg | " |
| Example 17 | 0.002 mg | 100% |
| Example 18 | 0.004 mg | " |
| Example 19 | 0.01 mg | " |
| Example 24 | 0.004 mg | " |

-continued

|  | Kill rate |  |
|---|---|---|
| Comparative agent I | 0.02 mg | 100% |
|  | 0.01 mg | <80% |
| Comparative agent II | 0.05 mg | 100% |
|  | 0.02 mg | <80% |

6. Contact action on ticks (Ornithodorus moubata)

The experiment is carried out on ticks which have sucked blood only once. Commercially available teabags, each containing 5 animals, are dipped for 5 seconds in the aqueous active ingredient formulations. The bags are then suspended. The kill rate is determined after 48 hours.

The temperature is kept at 25°–26° C.

Results:

|  |  | Dill rate |
|---|---|---|
| Example 1 | 4 ppm | 100% |
| Example 2 | 100 ppm | " |
| Example 5 | 40 ppm | " |
| Example 8 | 40 ppm | " |
| Example 9 | 10 ppm | " |
| Example 12 | 20 ppm | " |
| Example 16 | 1 ppm | " |
| Comparative agent I | 400 ppm | 100% |
|  | 200 ppm | <80% |
| Comparative agent II | 1,000 ppm | 100% |
|  | 400 ppm | <80% |

We claim:

1. An oximinophosphoric acid derivative of the formula I $$\begin{array}{c} R^1O \diagdown \overset{X}{\underset{\|}{P}} -O-N=C-\underset{\underset{CN}{\overset{|}{C}}}{\overset{CH_3}{\underset{|}{C}}}-S-R^3, \\ R^2 \diagup \end{array} \quad (I)$$

where $R^1$ is straight-chain or branched alkyl of not more than 4 carbon atoms, $R^2$ is straight-chain or branched alkoxy or alkylthio, each of not more than 4 carbon atoms, straight-chain or branched alkyl of not more than 3 carbon atoms, phenyl, amino, or straight-chain or branched alkylamino or dialkylamino, where alkyl in each case is of not more than 4 carbon atoms, $R^3$ is straight-chain or branched alkyl of not more than 4 carbon atoms and X is oxygen or sulfur.

2. An oximinophosphoric acid derivative of the formula I, as defined in claim 1, wherein $R^1$ is ethyl, $R^2$ is ethoxy, X is S and $R^3$ is methyl.

3. An oximinophosphoric acid derivative of the formula I, as defined in claim 1, wherein $R^1$ is methyl, $R^2$ is methoxy, X is S and $R^3$ is methyl.

4. An oximinophosphoric acid derivative of the formula I, as defined in claim 1, wherein $R^1$ is ethyl, $R^2$ is ethoxy, X is S and $R^3$ is ethyl.

5. An oximinophosphoric acid derivative of the formula I, as defined in claim 1, wherein $R^1$ is methyl, $R^2$ is methoxy, X is S and $R^3$ is ethyl.

6. A process for controlling pests, wherein an effective amount of an oximinophosphoric acid derivative as defined in claim 1 is allowed to act on pests or on their habitat.

7. A pesticide containing a solid or liquid carrier and an effective amount of one or more oximinophosphoric acid derivatives of the formula I as claimed in claim 1.

* * * * *